United States Patent
Feldman et al.

(10) Patent No.: US 6,452,177 B1
(45) Date of Patent: Sep. 17, 2002

(54) ATMOSPHERIC ELECTRON X-RAY SPECTROMETER

(75) Inventors: Jason E. Feldman, Pasadena; Thomas George, La Crescenta; Jaroslava Z. Wilcox, Los Angeles, all of CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 09/390,547

(22) Filed: Sep. 3, 1999

Related U.S. Application Data (60) Provisional application No. 60/099,185, filed on Sep. 4, 1998.

(51) Int. Cl.$^7$ ................... H01J 37/256; G01N 23/225
(52) U.S. Cl. ................. 250/310; 250/307; 250/441.11
(58) Field of Search .................. 250/310, 441.11, 250/307

(56) References Cited

U.S. PATENT DOCUMENTS

| | | | | |
|---|---|---|---|---|
| 2,908,821 A | * | 10/1959 | Schumacher | 250/310 |
| 4,988,872 A | * | 1/1991 | Nagatsuka et al. | 250/310 |
| 5,391,958 A | | 2/1995 | Kelly | |
| 5,430,292 A | * | 7/1995 | Honjo et al. | 250/310 |
| 5,478,266 A | | 12/1995 | Kelly | |
| 5,619,589 A | | 4/1997 | Otsu et al. | 386/160 |

FOREIGN PATENT DOCUMENTS

| JP | 4-133253 | * | 7/1992 | 250/441.11 |
|---|---|---|---|---|

OTHER PUBLICATIONS

N. Baumgarten, "The environmental scanning electron microscope (SEM) eliminates the high–vacuum requirement of conventional SEM, allowing the analysis of unprepared, wet samples" Nature, Sep. 7, 1989, pp. 81–82, vol. 341.

J. Beatty, et al., "A new miniature x–ray device for interstitial radiosurgery: Dosimetry", Medical Physics, Jan. 1, 1996, pp. 53–62, vol. 23, No. 1.

A. Castellano, et al., "A portable instrument for energy–dispersive X–ray fluorescence analysis of sulfur", Nuclear Instruments and Methods in Physics Research B, 1997, pp. 281–283, vol. 129.

G.D. Danilatos, "Design and Construction of an Atmospheric or Environmental SEM (Part 3)", Scanning, 1985, (17 pgs.), vol. 7, No. 1.

G.D. Danilatos, "Equations of Charge Distribution in the Environmental Scanning Electron Microscope (ESEM)", Scanning Microscopy, 1990, pp. 799–823, vol. 4, No. 4, Scanning Microscopy International, Chicago, IL.

G.D. Danilatos, "Introduction to the ESEM Instrument", Microscopic Research and Techniques, 1993, pp 354–361, Wiley–Liss, Inc.

M. Dinsmore, et al., "A new miniature x–ray source for interstitial radiosurgery: Device description", Medical Physics, Jan. 1, 1996, pp. 45–52, vol. 23, No. 1.

B.L.Doyle, et al., "External micro–ion–beam analysis (X–MIBA)", Nuclear Instrument and Methods in Physics Research, B54, 1991, pp. 244–257.

(List continued on next page.)

*Primary Examiner*—Jack Berman
(74) *Attorney, Agent, or Firm*—Christie, Parker & Hale, LLP (57) ABSTRACT

The present invention comprises an apparatus for performing in-situ elemental analyses of surfaces. The invention comprises an atmospheric electron x-ray spectrometer with an electron column which generates, accelerates, and focuses electrons in a column which is isolated from ambient pressure by a:thin, electron transparent membrane. After passing through the membrane, the electrons impinge on the sample in atmosphere to generate characteristic x-rays. An x-ray detector, shaping amplifier, and multi-channel analyzer are used for x-ray detection and signal analysis. By comparing the resultant data to known x-ray spectral signatures, the elemental composition of the surface can be determined.

20 Claims, 7 Drawing Sheets

OTHER PUBLICATIONS

T. George, "Miniature Electron Microscopes Without Vacuum Pumps", NASA Tech Briefs, Aug. 1998, pp. 38, 40.

E.D. Green, "Atmospheric Scanning Electron Microscopy," PhD Dissertation, Dept. of Electrical Engineering, Stanford University, J. Vac. Sci. Technol. B, 9 (3), 1992, pp. 1–112.

E.D. Green, "Atmospheric scanning electron microscopy using silicon nitride thin film windows," J. Vac. Sci. Technol. B, May/Jun. 1991, pp. 1557–1558, vol. 9, No. 3.

E.D. Green, et al., "Theoretical model for scanning electron microscopy through thin film windows", J. Vac. Sci. Technol. B, Nov./Dec. 1991, pp. 3070–3073, vol. 9, No. 6.

Rieder, et al., "Determination of the chemical composition of Martian soil and rocks: The alpha proton X ray spectrometer", Journal of Geophysical Research, Feb. 25, 1997, pp. 4027–4044, vol. 102, No. E2.

* cited by examiner

ATMOSPHERIC ELECTRON X-RAY SPECTROMETER

RELATED APPLICATIONS

This application is based on provisional patent application Serial No. 60/099,185 filed Sep. 4, 1998.

GOVERNMENT LICENSE RIGHTS

The U.S. Government has certain rights in this invention pursuant to NAS7-1407 awarded by NASA.

BACKGROUND OF THE INVENTION

The invention is an atmospheric electron x-ray spectrometer. More specifically, the invention is an apparatus for performing in-situ elemental analysis of surfaces.

Prior methods used to perform in-situ elemental analysis, such as alpha proton x-ray spectroscopy and x-ray excited fluorescence have very long spectrum acquisition times. Acquiring a spectrum from a sample has taken several hours using systems in the prior art. Further, the methods used by prior art systems have been limited to analyzing large surface areas of a sample.

Thus, there is a need for a miniature, portable instrument capable of rapidly conducting in-situ elemental analysis of samples by using a compact, low power, for example battery power, instrument.

There is further a need for such a system for determining the chemical and elemental composition of soil and rocks in remote locations not easily accessible by humans, such as in deep wells bored for oil exploration or on Mars and other planetary bodies. Such an instrument must be of minimal size and mass, and for planetary exploration applications, must have a low energy requirement so that the instrument may be included on planetary landing craft.

SUMMARY OF THE INVENTION

The above problems are solved by the present invention, which comprises an apparatus for performing in-situ chemical and elemental analysis of surfaces. The invention comprises an atmospheric electron x-ray spectrometer containing an evacuated electron column which generates, accelerates, and focuses electrons and is isolated from the ambient atmosphere by a thin, electron transparent membrane. After passing through the membrane, the electrons impinge on the sample in atmosphere to generate characteristic x-rays. These x-rays are detected and analyzed using a detection system consisting of a solid-state, positive-intrinsic-negative (PIN) diode coupled with an amplifier and a multi-channel analyzer. The output of the x-ray detection system is an x-ray spectrum, which can be analyzed to determine the elemental composition of the surface.

The characteristic x-rays are excited and analyzed to determine the sample elemental composition as in a conventional electron microscope, without the need to introduce the sample into vacuum. The approximately 1 kg instrument may require less than 50 J per acquired spectrum, with a spatial resolution of less than 1 mm and a spectrum acquisition time of less than 1 minute. This rapid analysis capability coupled with the low energy consumption of the instrument enables several terrestrial in-situ measurement applications requiring portable instruments as well as for short duration experiments on space missions with severe constraints on mass and energy resources, and allows, rapid, multiple composition measurements to be made. The high spatial resolution measurements of the surface elemental composition of individual samples made with the instrument will have terrestrial benefits and may also further space exploration program goals to assess the mineralogical and biological state and evolutionary history of pristine or prepared planetary samples.

The electron column employed by the atmospheric electron x-ray spectrometer is that currently used in television tubes, and it can be miniaturized further by microfabrication techniques based largely on the micromachining of silicon. In this embodiment, the electron column comprises stacked wafers, or chips, assembled in a vacuum using a wafer-to-wafer bonding approach. The chips have metal-film apertures that serve as electrodes for accelerations, deflection, and to focus the electron beam through the electron transparent membrane and onto the sample.

The x-ray detector for the apparatus is mounted outside the vacuum and near the sample to capture the spectral signature of the sample.

The invention can be utilized as a sub-kilogram, in situ instrument enabling rapid, quantitative elemental analysis of planetary surfaces. The instrument falls in the same class of miniature in-situ x-ray fluorescence instruments such as the alpha proton x-ray spectrometer (APXS) and other commercially available x-ray induced fluorescence (XRF) instruments. Unlike those systems, the atmospheric electron x-ray spectrometer offers significantly faster spectrum acquisition, much higher spatial resolution, and shorter sampled depth in comparison to the other elemental analysis techniques. These features enable new types of observations of planetary surfaces that were not possible previously.

One feature is a small irradiated spot size. An instrument providing a 100 $\mu$m to several mm spot size on the irradiated sample is able to determine local elemental composition of rocks and soil, which has not yet been achieved on another planet. For comparison, the Pathfinder alpha-proton x-ray spectrometer measured a spot about 4 cm in diameter. The small spot size is particularly effective when used in combination with other instruments, such as high resolution imaging systems boresighted with the electron beam. Elemental composition measurements will provide important clues on the temperature, pressure, and other properties relevant to formation and modification conditions of the rock and soil. For example, the amount of Ca, Mg, and Fe in pyroxene, or Fe, Ti, and other cations in iron oxides can be determined.

Another feature is a rapid spectrum acquisition. Short spectrum acquisition times (resulting in low energy consumption) will enable rapid multiple readings of a sample. Alternatively, the invention can be used to rapidly scan several samples, effectively providing a quick look, elemental surface analysis of a region.

Another feature is a short penetration depth into the sample for the electron beam. The $\mu$m-scale penetration depth will allow surface coatings and weathering rinds on rocks to be measured with minimal mixing effects from deeper material. Measurements of unaltered surfaces will require prompt sampling of freshly cored or broken rocks, activities that are planned in several future Mars sampling inissions, which can be accomplished by the invention.

The planned reductions in the size of future spacecraft will potentially result in reductions in payload capacity. Therefore, to maximize the science return it is extremely important to develop a suite of highly capable miniature instruments. The atmospheric electron x-ray spectrometer satisfies this need in the area of elemental analysis. One of the most important in situ measurements is the determination of the composition of planetary bodies and remnant planetary building blocks such as comets and asteroids. These measurements can also provide information on pre-biotic chemistry in the solar system. X-ray fluorescence techniques provide a non-contact method of determining the elemental composition. When a material is irradiated by high-energy α-particles, x-rays, or electrons, it emits an x-ray spectrum that consists of characteristic peaks for the individual elements (plus a broad background). By using suitable spectrum analysis techniques, not only can the elemental composition be identified but also the mass fractions of the individual elements can be determined to within a few percent. This technique has proved invaluable for determining the chemical make-up of a planetary body, and all in situ missions, including the US Viking 1&2, Mars Pathfinder, and Soviet Venera missions, have carried some form of x-ray fluorescence instrument.

BRIEF DESCRIPTION OF THE DRAWINGS

For a fuller understanding of the invention, reference is made to the following description taken in connection with the accompanying drawings, in which.

DETAILED DESCRIPTION OF THE PREFERRED EMBODIMENTS

Figure 1:
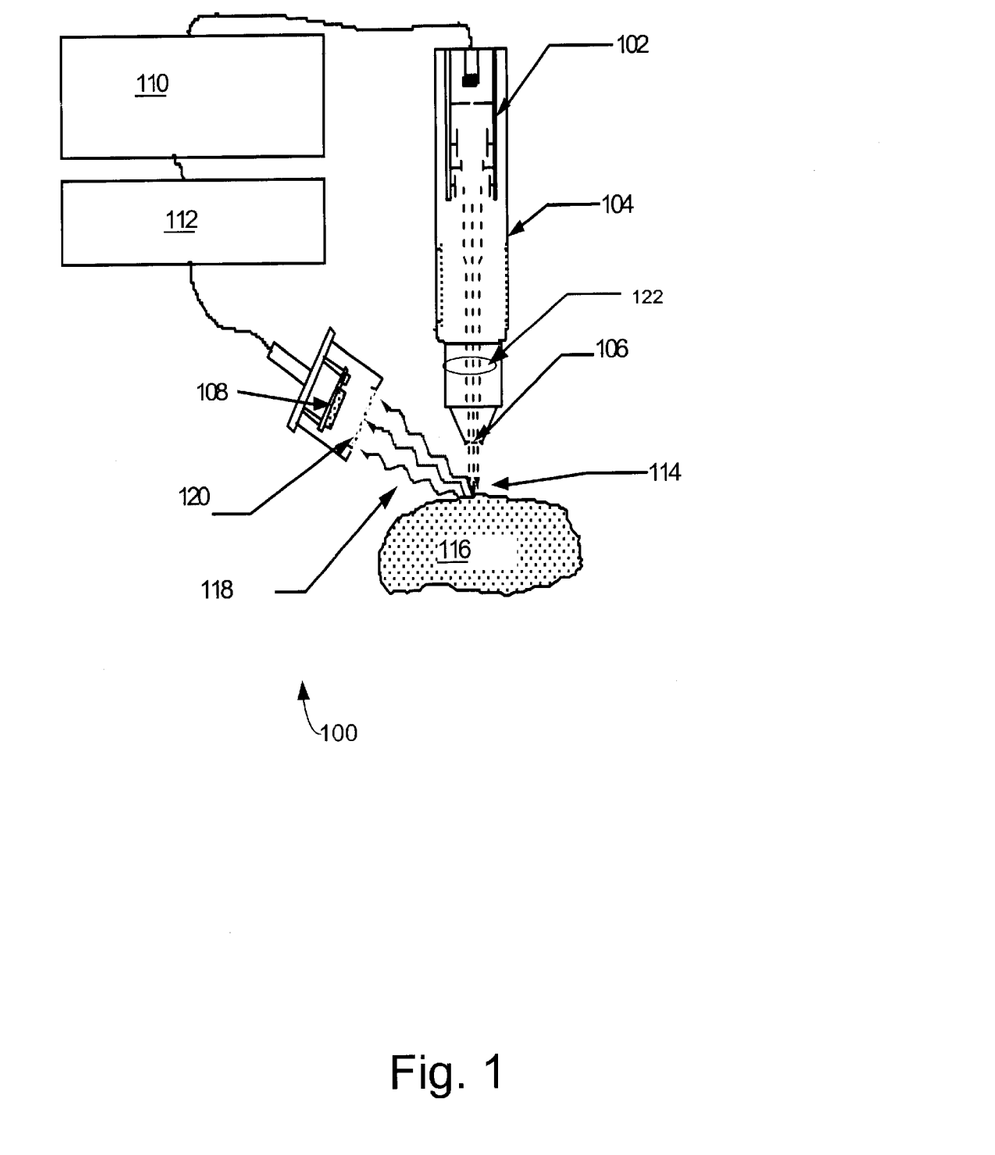
FIG. 1 illustrates a structural diagram of the atmospheric electron x-ray spectrometer of the present invention.

With reference to FIG. 1, a structural diagram of the system of the present invention is shown. The atmospheric electron x-ray spectrometer (AEXS) 100 is comprises an electron source or column 102 encapsulated in a vacuum enclosure 104 by an electron transmissive membrane 106, an energy dispersive x-ray (EDX) detection system 108, a high voltage power supply (HVPS) 110, and a control electronics box 112. The electron column 102 may comprise a commercially available electron tube (SONY part #FM2210) by CRT Scientific Co. The x-ray. detector 108 is a silicon PIN photodiode-based system, having a receptive ultra-thin membrane x-ray window 120, developed by Amptek Inc. (part #XR-100CR) 120 and used for the Mars Pathfinder alpha-proton x-ray spectrometer instrument.

The electron column 102 includes an electron emitter and electrostatic optics. An electron beam 114 is generated by a thermoionic emitter, or possibly a field emitter, accelerated to a high energy in excess of 15 keV, and focused by column optics on the encapsulating membrane 106. The electron beam 114 transmitted through the membrane 106 impinges on a sample 116 located outside the membrane 106, in the planetary atmosphere. Characteristic x-rays 118 are generated from the irradiated portion of the sample 116. The electrons 114 also ionize the planetary atmosphere, ensuring a return current path. The elemental chemical composition of the irradiated spot is determined by collecting and analyzing the generated x-rays using the EDX detector 108.

The thin electron transmissive membrane 106 comprises a thin electron transmissive membrane material of silicon, boron nitride, or other low Z (average atomic number) and low density material, which those skilled in the art of electron transmission through thin membranes would recognize as causing low levels of electron scattering. For example, the membrane 106 may comprise a 200 μm thick SiN membrane of about 2 mm$^2$ area, which has been selected as the baseline membrane for one instrument 100 prototype. The membrane 106 is mounted to the end of the vacuum enclosure 104. The membrane 106 serves to isolate the vacuum inside the enclosure from the ambient atmosphere.

In one embodiment of the vacuum enclosure 104, an ion pump 122 is further included. The ion pump 122 could be employed to help maintain the vacuum in the vacuum enclosure 104, and to protect against gas diffusion through the membrane 106 as well as gas leaks into the vacuum enclosure 104. The ion pump 122 is operated as necessary to maintain a vacuum sufficient for operation of the electron column in the vacuum enclosure 104 which may comprise a sealed glass tube with electrical feedthroughs as a single sealed unit with the membrane 106. The ion pump 122 is an electrostatic getter ion pump which utilizes the electrons from the electron column to ionize gas molecules, which are subsequently accelerated and deposited onto a getter surface. The ion pump 122 is described in more detail in the NASA New Technology Report, NPO-20436, by J. Wilcox, T. George and J. Feldman, entitled, "Miniaturized Ring Orbitron Getter-Ion Pump".

The high voltage power supply 110 uses a flyback voltage converter working in conjunction with a Cockroft-Walton type voltage multiplier to implement a high-frequency switch mode power converter. The power supply 110 is battery operated and provides up to 40 kV to the electron column 102, as well as lower voltages to the ion pump 122 and the other associated circuit elements described herein.

The control electronics box 112 comprises electronics to switch on and off the electron column 102, ion pump 122, and x-ray detection system 108.

Figure 2:
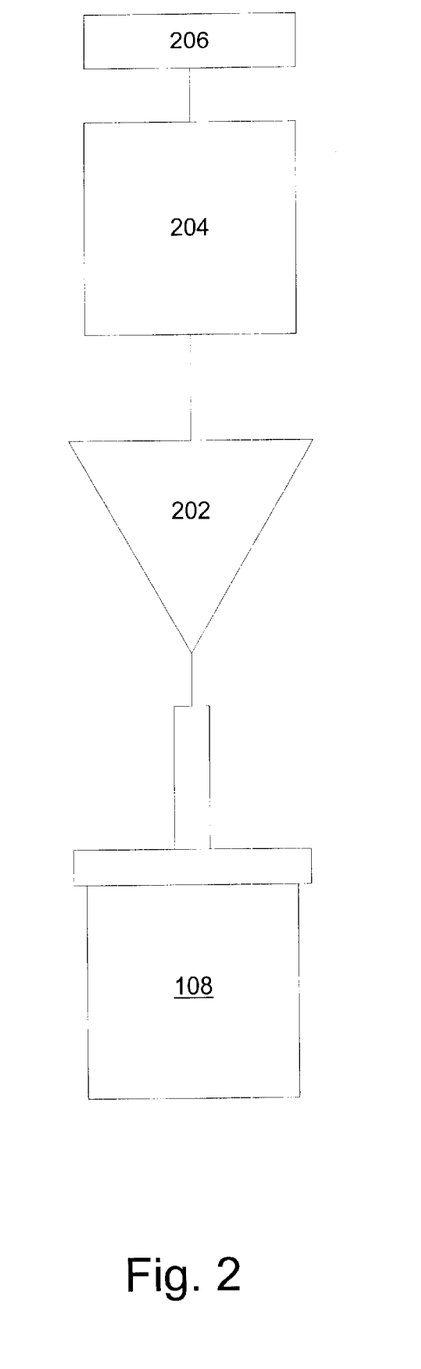
FIG. 2 illustrates further components of the spectrometer of FIG. 1.

With reference to FIG. 2, a diagram illustrating further components of the instrument 100 illustrated of FIG. 1 is shown. The x-ray detector 108 is electrically connected to a signal conditioning amplifier 202 which accepts the output of the x-ray detector and produces a Guassian pulse suitable for input to a miniaturized multi-channel analyzer 204 similar to standard multi-channel analyzers known in the art and used in laboratories. The x-ray detector 108 is electrically connected to the multi-channel analyzer for transmission of the Guassian pulse. A computer with a data acquisition board 206 is electrically connected to the multi-channel analyzer 204 for processing and transmitting the resulting spectrograph from the instrument. Alternatively, the multi-channel analyzer 204 may comprise a display screen for displaying data and/or a spectrograph.

All of the components described above may be contained in a portable instrument enclosure which can be brought to the sample to be analyzed.

Figure 3:
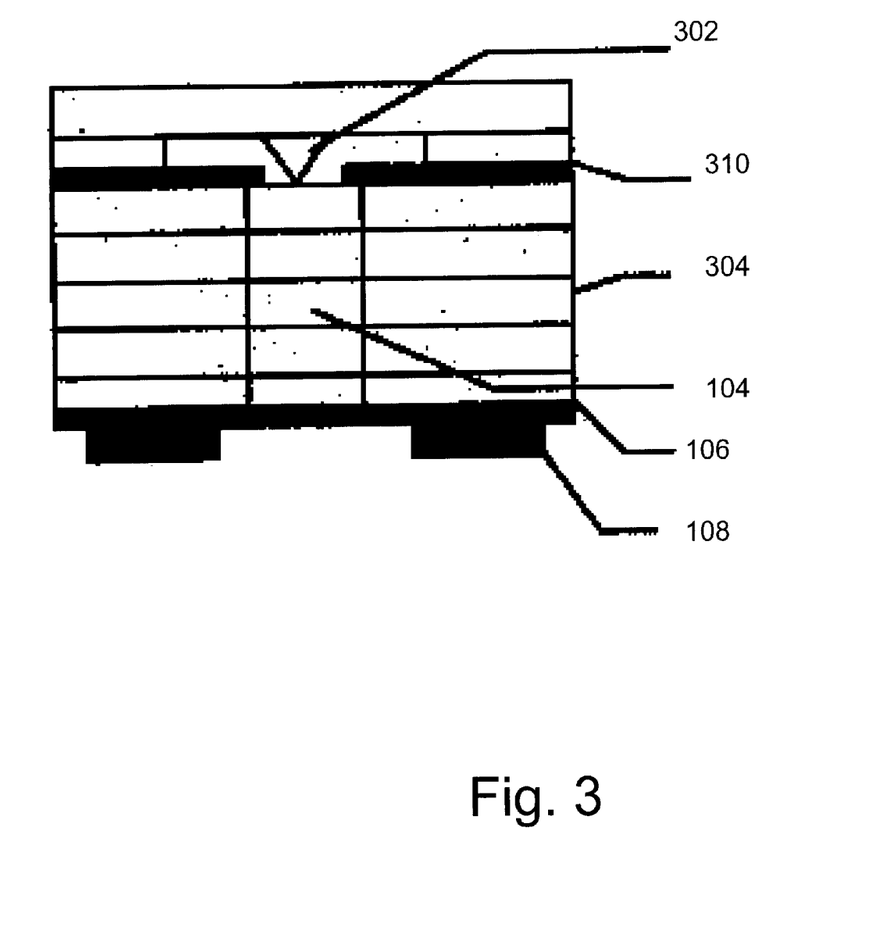
FIG. 3 illustrates an alternative electron column for use with the spectrometer of FIG. 1.

With reference to FIG. 3 an alternative atmospheric electron x-ray spectrometer is configuration is shown. The alternative atmospheric electron x-ray spectrometer makes use of micro electromechanical systems (MEMS) technology to achieve significant reduction in size, mass, and power consumption. The microfabricated atmospheric electron x-ray spectrometer comprises a much smaller evacuated enclosure 104, an electron source 302 at a first end of the enclosure 104 surrounded by a gate electrode 310, and the electron-transparent membrane 106 mounted at a second end of the enclosure 104 opposite the electron source 302. The evacuated enclosure 104 is a few millimeters thick and about a centimeter square. Enclosure 104 is formed by a stack of high-voltage acceleration deflection, and focusing electrodes comprising microfabricated chips 304 with metal-film apertures.

The electrical source 302 is either thermionic or an assembly of field emitters, depending on the vacuum level of evacuated enclosure. In order to maintain the vacuum, an ion pump 122 like that shone in FIG. 1 may further be included. Although some field-emission sources require ultra-high vacuum (around $10^{-10}$ torr) for operation, the development of diamond-based field emitters requires much less stringent vacuum requirements (as low as $10^{-4}$ torr) for operation and could be better suited for use as the electron source 302.

The atmospheric electron x-ray spectrometer configuration in FIG. 3 mnay further include one or more of the x-ray detectors. 108 mounted outside the electron column 100 in close proximity to the membrane 106.

Figure 4A:
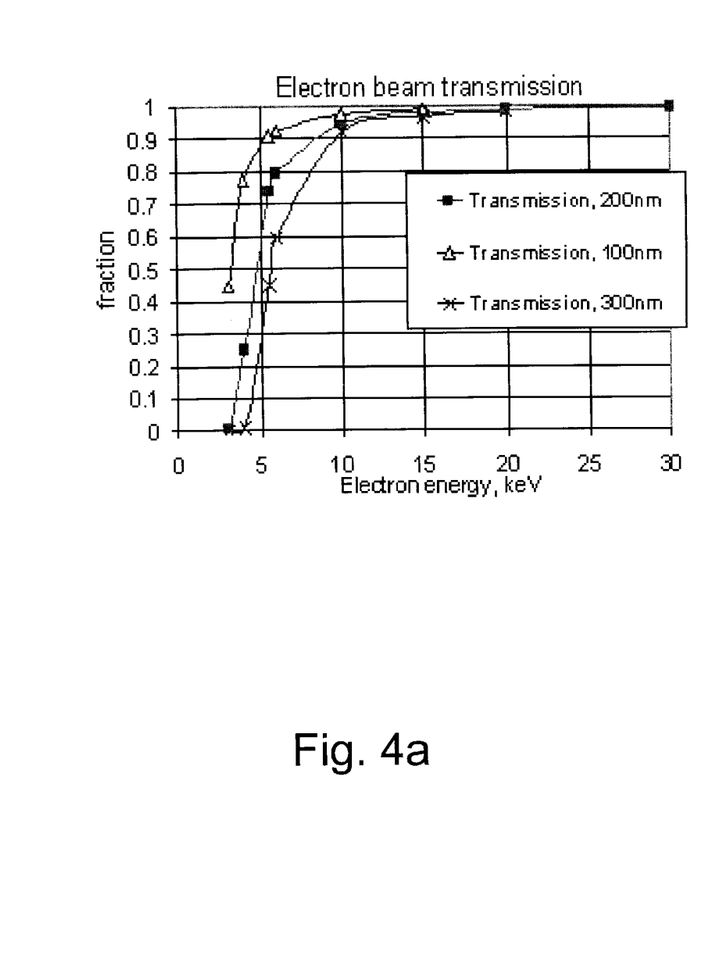
FIGS. 4a–4b, illustrate two graphic plots from a theoretical model showing predicted electron transmission properties of SiN membranes for the spectrometer of FIG. 1.
Figure 4B:
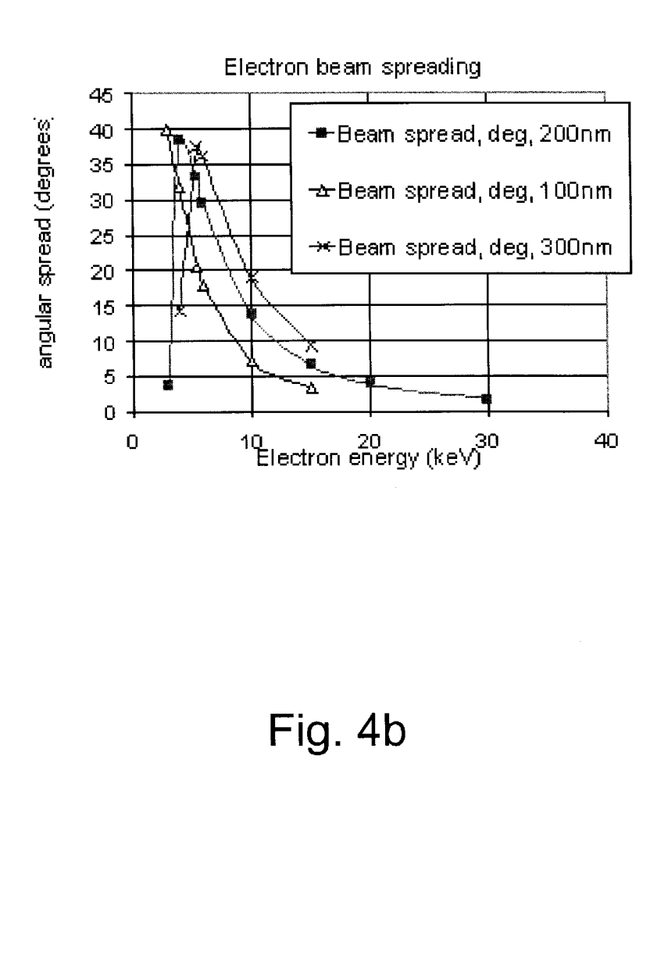

With reference to FIGS. 4a–4b, two graphical plots showing mathematically simulated electron transmission properties of SiN type membranes 106 are shown for the atmospheric electron x-ray spectrometer 100 operation. Electron transmission through the membrane 106 is shown as a function of the electron energy, membrane 106 thickness, and membrane 106 composition (SiN, BN) based on Monte Carlo simulations. The simulations indicate that attenuation and spreading of the electron beam are even less than that predicted by standard scattering formulas. The electron transmission is greater than 90%, and the angular spread is less than 13 degrees for 10 keV electrons (the transmissivity is 98% and beam spread less than 7 degrees for 15 keV electrons) for a 200 nm thick SiN membrane. The experimental results were consistent with predictions for 5.5 keV.

Figure 4C:
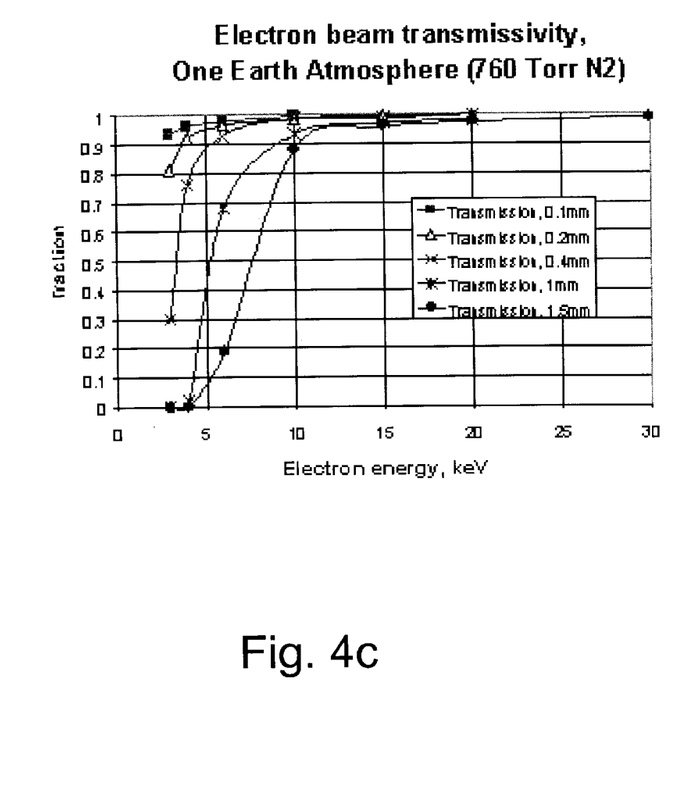
FIGS. 4c–4d, illustrate two graphic plots from a theoretical model showing predicted electron transmissive properties through one Earth atmosphere for the spectrometer of FIG. 1.
Figure 4D:
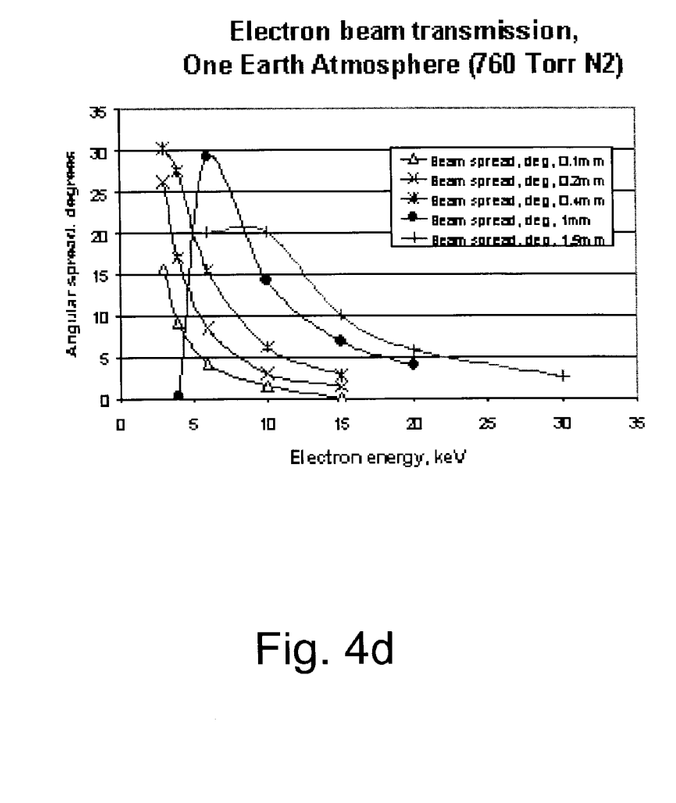

With reference to FIGS. 4c–4d, two plots of predicted transmission properties of the electron beam in one Earth atmosphere are shown. Before impinging on a sample 116 (FIG. 1), the electrons transmitted through the membrane 106 travel a short "working distance" through the atmosphere where they are subject to atmospheric electron scattering. These atmospheric scattering effects are considerably less than in the membrane 106, with the proportion being roughly dependent on the ratio of their average atomic number (Z) densities. For example, this ratio for the SiN to the atmosphere densities is about $2 \times 10^7$. The irradiated spot size on the sample is determined by beam spreading in both the membrane and atmosphere. The beam spreading can be minimized by using thin membranes 106, short working distances and using high energy electrons. As shown in FIGS. 4a–4d, beam spreading is nearly always dominated by membrane-induced spreading. Atmospheric scattering effects will broaden a 30 keV electron beam from a point source to a spot size of 1 mm at a 2 cm working distance. The spot size has a geometrical dependence on the working distance, becoming smaller with shorter working distances. The membrane 106 was shown in prototype laboratory tests at the Jet Propulsion Laboratory to be able to easily withstand one Earth atmosphere of differential pressure. The membrane 106 heating by the electron beam was also modeled. The predicted temperature Lo increase was less than 150 C. when irradiated by an electron beam with the currently baselined parameters (10 $\mu$A at 15 keV). The heating; effects are smaller for lower beam currents and/or higher beam energies.

The electron-transmissive membrane 106 is the critical component of the instrument 100 and can be fabricated using Si microfabrication technology. Currently a 200 nm thick, CVD-deposited low-stress SiN film is used as the membrane. The membrane 106 sealing technology can be derived from proven solutions developed for research and industrial applications. One such membrane mounting system has been developed and described in U.S. Pat. No. 5,391,958.

The following table compares the predicted performance for the atmospheric electron x-ray spectrometer 100 with prior in situ x-ray fluorescence based instruments, namely the alpha-proton x-ray spectrometer (APXS), described in R. Reider, H. Wanke, T. Economou, and A. Turkevich, "Determination of the chemical composition of Martian soil and rocks: The alpha proton X ray spectrometer", J. Geophysical Research, 102, No, E2, pp. 4027–4044, (1997), and a proposed x-ray induced fluorescence (XRF) instrument. The alpha-proton x-ray spectrometer was operated successfully on Mars Pathfinder as a part of the Sojourner rover payload. Miniature x-ray induced fluorescence instruments are currently in development by several collaborative groups, typically employing an x-ray tube to provide excitation x-rays.

| property | | AEXS 100 (present) invention) | XRF (proposed) | APXS (flight) |
|---|---|---|---|---|
| Mass[1] | | 970 g | 1000 g | 570 g |
| Source[2] | Excitation particle | Electrons | x-ray photons | α-particles |
| | Flux | $6 \times 10^{13}$/s (10 $\mu$A) | $2 \times 10^{12}$/s | $2 \times 10^9$/s (50 mCi) |
| | Power | 5 W (current HVPS) | 13 W | 0.34 w |
| Excitation efficiency[3] | X-ray photons emitted per particle | $5 \times 10^{-6}$ | $1.4 \times 10^{-5}$ | $5 \times 10^{-6}$ |
| | Geometrical efficiency | $>10^{-4}$ | $10^{-6}$ to $10^{-5}$ | $10^{-4}$ |
| | X-ray photons per second | $>2 \times 10^{-4}$ | $10^2$ to $10^3$ | ~1 |
| Spectrum acquisition[4] | Acquisition time | 10 seconds | 5 minutes | 10 hours |
| | Energy per acquisition | 50 J | 5,000 J | 10,000 J |
| Spot size[5] | Controlled by beam focusing | $10^{-2}$ to $10^{-4}$ cm$^2$ (spot size from 100 $\mu$m to several mm) | ~4 cm$^2$ (2 cm working distance) | ~20 cm$^2$ |

For the atmospheric electron x-ray spectrometer 100 most of the power is consumed by the high voltage power supply 110; optimization of the atmospheric electron x-ray spectrometer configuration will reduce this figure to about 2 W. Conversely, for the x-ray induced fluorescence instrument, the primary current must be high (0.3 A) to make up for losses due to the low ($10^{-3}$) electron/x-ray conversion efficiency; the accelerator column consumes in excess of 9 W vs. 4 W for the emitter.

The excitation efficiency is the product of the fluorescence efficiency and the probability that the x-rays escape from the sample. The estimates are for Si samples irradiated by 30 keV electrons by the atmospheric electron x-ray spectrometer 100, an Au target for the x-ray induced fluorescence, and for 5 MeV α-particles for the alpha-proton x-ray spectrometer. The geometrical efficiency was estimated for each instrument assuming the same (approximately 4 mm$^2$) x-ray detector area, about 2 cm working distance for the atmospheric electron x-ray spectrometer 100 and the x-ray induced fluorescence instrument, and 4 cm for alpha-proton x-ray spectrometer.

The above table shows that although the atmospheric electron x-ray spectrometer 100 is competitive with the other in-situ techniques in terms of instrument mass and power consumption, its real strength lies in the more than an order-of-magnitude improvements in the x-ray spectrum acquisition time and spatial resolution of the sampled spot. In comparison to the alpha-proton x-ray spectrometer, the atmospheric electron x-ray spectrometer 100 source is about $10^4$ times more intense. The higher intensity electron source has a predicted spectrum acquisition time of about 10 seconds as compared to 10 hours for the alpha-proton x-ray spectrometer and an energy consumption of about 50 Joules as compared to 10 kJ per spectrum. In comparison to an x-ray induced fluorescence instrument, the atmospheric electron x-ray spectrometer 100 uses the primary electrons more efficiently by directly exciting the characteristic x-rays, an increase in x-ray generation efficiency by a factor of about $10^3$. The rapid spectrum acquisition enables a high science return, and the consequent tremendous savings in energy consumed per acquired spectrum makes efficient use of on-board energy resources. In addition to these savings, inherent to the atmospheric electron x-ray spectrometer 100 is the ability to focus the electron beam, enabling a much higher spatial resolution than the other techniques. Note also that the atmospheric electron x-ray spectrometer 100 is essentially a surface analysis technique due to the micrometer ($\mu$m)-scale penetration depth of the electrons.

The atmospheric electron x-ray spectrometer 100 is designed to be a miniature, non-contact, portable instrument requiring no external pumping or sample manipulation. The electron-transmissive membrane eliminates the need for samples to be drawn into the vacuum of the electron column. The ionization of the atmosphere provides a return path for the current so that non-conductive mineral samples do not need to be coated with a conductive material to prevent charging effects.

Due to the combined effect of a high electron flux and high x-ray conversion efficiency, a 10 $\mu$A beam current results in $2\times10^4$ x-ray photons collected by a 4 mm$^2$ area detector placed at 2 cm distance from the sample. Typically, using the high voltage power supply 110, the total energy consumption per spectrum (including power supply losses) is about 50 J. This consumption can be decreased through design optimization for the specific flight instrument created with the invention. Optimization of the high voltage power supply 110 has been predicted to reduce the power consumption to about 2 W, corresponding to an energy consumption of about 20 J per spectrum, with additional savings possible through column, sample, and detector optimization. It should be noted that charged particle excitation is preferred to any other (e.g. x-ray) excitation because it produces the best signal-to-noise ratio due to the absence of any Compton scattering. Thus fewer counts are required to resolve the x-ray spectrum.

The x-ray fluorescence generated by the atmospheric electron x-ray spectrometer 100 is detected and analyzed using the same techniques as the alpha-proton x-ray spectrometer and the x-ray induced fluorescence instruments. Whereas the radioactive source head dominates the mass budget for the alpha-proton x-ray spectrometer, the high voltage power supply 110 makes up the bulk of the atmospheric electron x-ray spectrometer 100 mass. Even with this unavoidable overhead, advances in the miniaturization of high voltage power supplies, as described in J. C. Geck Jr., "Slash High Voltage Supply Drain", Electronic Design Vol. 19, Sept. 13, (1974) and G. C. Chryssis, "High Frequency Switching Power Supplies," McGraw-Hill, N.Y. (1989), insures that the total mass of the instrument is competitive with the state-of-the-art alpha-proton x-ray spectrometer. Since the atmospheric electron x-ray spectrometer 100 sensor head is relatively low in mass, several sensor heads can be mounted simultaneously on a rover arm or elsewhere, and can be powered by the same power supply mounted on the rover chassis.

By using the thin membrane for the window of the x-ray detector 120, the cut-off energy of the accepted x-rays may be lowered from the present cutoff for the state-of-art 4 $\mu$m thick detector Be window. By lowering the energy cutoff, this replacement may enable the detection of light elements (such as C, N, and O), enabling identification of biologically significant minerals such as carbonates and nitrates, and assessment of the oxidation state of planetary surfaces.

Figure 5:
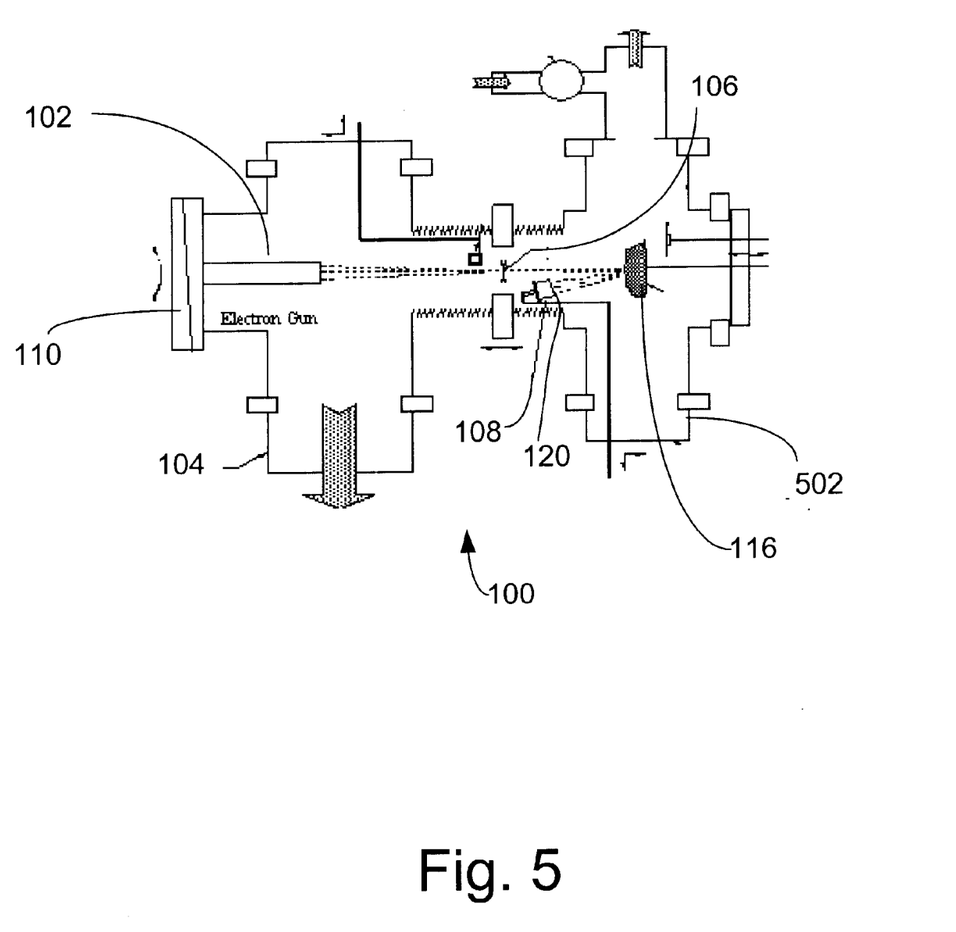
FIG. 5, illustrates a diagram. representing a laboratory test setup for the spectrometer of FIG. 1.

With reference to FIG. 5, a diagram representing a laboratory prototype of the atmospheric electron x-ray spectrometer 100 is shown. The laboratory atmospheric electron x-ray spectrometer 100 is operated with the electron column 102 biased at a large negative voltage and the membrane 106 (which serves as the final anode) at ground. Analysis has indicated that the Martian atmosphere will provide a sufficiently conductive ionization path for the return current. The electron column 102, procured from CRT Scientific Inc, is integrated into the modified test setup and operated using a programmable laboratory power supply 110 (FIG. 1) capable of independently biasing four electrostatic lens elements down to −30 kV.

The membrane 106 is mounted on a flange sealing the stainless steel vacuum enclosure 104 (volume ~4 cm$^3$) using H20E epoxy manufactured by Epoxy Technology of Billerica, Mass.

The x-ray fluorescence is detected using an Amptek XR-100 CR Si-PIN detector 108 with a 4 $\mu$m thick Beryllium window and a PX2CR amplifier. This system has a spectral resolution between 165 eV (24 $\mu$s dead time) and 200 eV (12 $\mu$s dead time) FWHM, which is somewhat better than the XR-100T Amptek detector system that was flown on Mars Pathfinder. The system includes a charge-sensitive preamplifier, a shaping secondary amplifier, power supplies, and (for field use) a multichannel analyzer. The characterization experiments include measurement of the electron beam current, electron energy distribution, beam spot size, and x-ray yield from the irradiated samples as a function of the electron optics, acceleration voltage, component configuration, and simulated atmospheric environment in a secondary chamber described below. The electron beam spot size is measured using either photographic densitometric techniques or imaged using a CCD camera. The flexible design of the test setup allows for rapid reconfiguration of the components independently of each other, and the electron-optical parameters such as acceleration voltage, beam current and focusing can be controlled with laboratory power supplies 110 and control electronics 112 as with the instrument 100 of FIG. 1. Finally, the x-ray emission spectra from the sample 116 is characterized.

The 4 $\mu$m thick Beryllium x-ray transmission window 120 supplied with the Amptek x-ray detector 108 cuts off characteristic x-rays from elements with atomic numbers less than 11 (Na). To enable detection of lighter elements, the energy cut-off can be lowered by substituting the window 120 with either a commercially available thin window or a thin membrane being similar to that of membrane 106. Geometrical effects have a significant role in the acquisition of the x-ray fluorescence spectra. The detector system 108 is integrated into the test setup 100 allowing for flexibility in positioning and investigation of configuration effects. Modeling and experimental verification of electron transmission through the membrane 106 and atmosphere yields the final spatial and energy distributions of the electron beam striking the target sample, which impacts the x-ray excitation.

The electron column 102 uses a high voltage power supply 110 and an isolated filament transformer. Ultravolt, Inc. has developed DC-to-DC converter modules supplying up to (+/−) 30 kV. For example, the model 30 A regulated DC-DC converter provides −30 kV at 0.13 mA in a Mil-C-5541 Class 1 package.

The laboratory test setup of the instrument 100 further comprises a secondary vacuum enclosure 502 for simulating different types of atmospheres, terrestrial and non-terrestrial, in addition to the vacuum enclosure 104 for the electron column 102. The secondary vacuum enclosure 502 is used to contain the sample 116 sealed therein. Thus, using the laboratory configuration of the instrument 100, different environments, such as the Martian atmosphere, may be simulated in the secondary vacuum enclosure so that the miniaturized version may be properly optimized for specific missions.

The operation of the laboratory atmospheric electron x-ray spectrometer as well as an x-ray data acquisition system is implemented via computer data acquisition and instrument control electronics system 112 with LabView software by the National Instruments Corporation of Austin, Tex.

The components of the laboratory embodiment of the present invention are listed in the table below together with other components which may be included with estimated weights of each component. From this list, a first-order estimate can be made of the mass (0.96 kg), volume (976 cm$^3$) and power consumption (6.8 W) of the breadboard AEXS. For the portable embodiment described above, these estimates are reduced by at least a factor of 2.

| Component | Manu-facturer | Function | Mass (kg) | Volume (cm$^3$) | Power (W) |
|---|---|---|---|---|---|
| Electron column 102 | CRT Scientific, Inc. | Electron Beam generation | 0.03 | 10 | ~1 |
| Membrane 106 | JPL | Electron transmissive vacuum-isolation | — | — | — |
| SiLi PIN detector 108 Power Supplies 110: | Amptek Inc. | x-ray detection | 0.001 | 1 | — |
| 30 kV supply (part of power supply 110) | NRL | Power supply for Electron accelerator Electron optics x-ray detector | 0.7* | 650* | 5* |
| Filament transformer (part of power supply 110) | NRL | Electron emitter power supply | 0.03 | 15 | ~0.5 |

-continued

| Component | Manu-facturer | Function | Mass (kg) | Volume (cm$^3$) | Power (W) |
|---|---|---|---|---|---|
| Preamplifier, Peak detector, Controller 112 | JPL | Signal analysis | 0.20 | 300 | 0.3 |
| Total | | | 0.961 | 976 | 6.8 |

The laboratory embodiment of instrument 100 is also used for calibration purposes with respect to samples in the simulated atmospheric conditions in the secondary vacuum enclosure 502. Natural samples are measured under various conditions to gauge the atmospheric electron spectrometer 100 suitability for in situ geologic analyses. The compositions measured by laboratory instrument 100 can be compared to bulk composition measurements provided by x-ray induced fluorescence powder analyses. Individual mineral grains with sizes >100 $\mu$m within rocks are measured by the instrument 100 and compared to mapped mineral measurements from a standard energy dispersive electron microprobe. Sample distances from the membrane 106 and incidence angle of the beam can thus be varied. For each sample, changes in the instrument 100 spot size and power can be assessed. Initial tests and calibration can be done under terrestrial and vacuum conditions. Further calibrations can then be conducted in a $CO_2$ atmosphere at extraterrestrial or Martian pressures.

The atmospheric electron x-ray spectrometer is calibrated to enable quantitative elemental composition analysis. Sources of noise and error as well as the instrumental 100 and environmental background. In situ calibration of the atmospheric electron x-ray spectrometer 100 is based on the large body of work on analytical electron microscopes and microprobes, including the peak-to-background method as described in V. D. Scott, G. Love, S. J. B. Reed, "Quantitative Electron-Probe Microanalysis", 2nd Edition, Ellis Horwood, N.Y. (1995).

Figure 6:
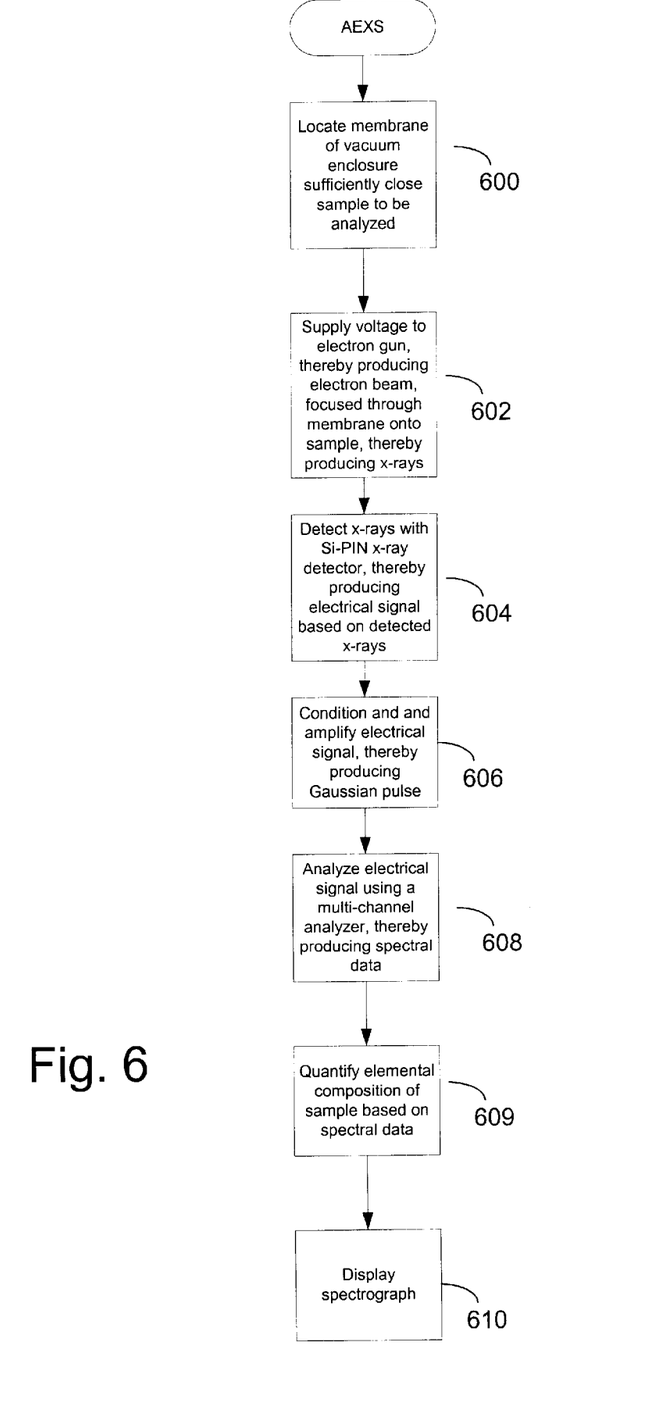
FIG. 6 is a flowchart illustrating the steps performed by the spectrometer of FIG. 1.

With reference to FIG. 6, a flow chart illustrating the steps for obtaining sample data for a sample 116 (FIG. 1) using the atmospheric electron x-ray spectrometer is shown. The sample and the membrane 106 of the vacuum enclosure 104 are located within sufficient close proximity to each other, step 600. Voltage is then supplied to the electron column 102 by the high voltage power supply (HVPS) 110, thereby producing an energetic electron beam focused through the electron transparent membrane 106 onto the sample 116, step 602. X-rays produced by the focusing of the electron beam on the sample are detected by the Si-PIN x-ray detector 108, thereby producing an electrical signal based on the detected x-rays, step 604. The electrical signal is amplified and conditioned, producing a Gaussian pulse, step 606. The gaussian pulse is analyzed using the multi-channel analyzer 204, thereby producing spectral data, step 608. The elemental composition of the sample may then be qualified based on the spectral data, step 609. The spectral data may then be displayed on a display means 206, which may comprise a cathode ray tube or similar device, step 610. The display format may comprise a visual representation of a spectrograph, sample composition list data, plot graphs or other types of scientific informational formats.

It will thus be seen that changes may be made in carrying out the above system and method and in the construction set forth without departing from the spirit and scope of the invention, it is intended that any and all matter contained in the above description and shown in the accompanying drawings shall be interpreted as illustrative and not in a limiting sense.

What is claimed is:

1. An atmospheric x-ray spectrometer comprising:
   a chamber isolated from the atmosphere by a gas impermeable electron transparent membrane to form a vacuum therein;
   an electron source arranged within the chamber for projecting a focused electron beam through the membrane onto an in-situ sample, thereby causing x-rays to be generated according to the composition of the sample;
   an atmospheric x-ray detector arranged outside the chamber for detecting the x-rays in-situ, thereby producing an electrical signal comprising an x-ray signature for the sample; and
   an analyzer electrically connected to the x-ray detector for identifying the composition of the sample by analyzing the x-ray signature for the sample.

2. The spectrometer of claim 1, wherein the chamber defines an elongated enclosure, the electron source being enclosed therein at one end of the evacuated enclosure and the gas impermeable electron transparent membrane arranged at an opposite end such that the electron beam is focused through the vacuum and the membrane onto the sample located outside the chamber.

3. The spectrometer of claim 2, further comprising an ion-pump within the enclosure for maintaining the vacuum.

4. The spectrometer of claim 1, further comprising a shaping amplifier electrically connected between the x-ray detector and the analyzer for amp ing and conditioning the electrical signal.

5. The spectrometer of claim 1, wherein the analyzer is designed to identify the composition of the sample by comparing the x-ray signature for the sample to a known x-ray signature of a known composition.

6. The spectrometer of claim 1, comprising a display electrically connected to the analyzer.

7. The spectrometer of claim 6, wherein the analyzer is designed to identify the composition of the sample by creating a spectrograph from the x-ray signature for the sample.

8. The spectrometer of claim 7, wherein the display is designed to display the spectrograph.

9. The spectrometer of claim 1, further comprising an electron column comprising a stack of high-voltage acceleration, deflection, and focusing electrodes, the electrodes having apertures forming an evacuated enclosure, wherein the electron source is arranged at one end of the evacuated enclosure and the electron transparent membrane is arranged opposite the electron source such that it seals the evacuated enclosure, wherein the electron beam is focused through the evacuated enclosure and the membrane onto the sample located outside the evacuated enclosure.

10. The spectrometer of claim 9, wherein the stack of high-voltage electrodes comprises a microfabricated stack of high-voltage acceleration, deflection, and focusing electrodes.

11. The spectrometer of claim 1, wherein the membrane is made of one of either SiN or BN.

12. The spectrometer of claim 1, wherein the electron beam can be focused to a spot having a size of about 100 $\mu$m.

13. The spectrometer of claim 1, wherein the x-ray detector is an energy dispersive x-ray detector.

14. The spectrometer of claim 1, wherein the electron source is one of either a thermionic source or an assembly of field emitters source.

15. A method for determining the surface composition of a sample in-situ, comprising the steps of:
    generating an electron beam in vacuum;
    focusing the electron beam through a gas impermeable electron transparent membrane onto the sample in-situ, thereby producing x-rays;
    detecting the x-rays with an atmospheric x-ray detector, thereby producing an electrical signal based on the detected x-rays;
    and analyzing the electrical signal, thereby identifying the surface composition of the sample in-situ.

16. The method of claim 15, further comprising reading an x-ray signature for the sample from the electrical signal.

17. The method of claim 16, further comprising comparing the x-ray signature for the sample to a plurality of known x-ray signatures.

18. The method of claim 17, further comprising identifying the composition of the sample by matching one of the known x-ray signatures to the x-ray signature for the sample.

19. The method of claim 18, further comprising creating a spectrograph representing the x-ray signature of the sample.

20. The method of claim 19, further comprising displaying the spectrograph.

* * * * *